United States Patent
Morehouse, III

(10) Patent No.: US 9,500,637 B2
(45) Date of Patent: Nov. 22, 2016

(54) FUEL WATER SEPARATOR BOWL WITH AN INTERNAL INSPECTION LIGHT

(71) Applicant: CATERPILLAR INC., Peoria, IL (US)

(72) Inventor: Darrell Lee Morehouse, III, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 173 days.

(21) Appl. No.: 14/450,081

(22) Filed: Aug. 1, 2014

(65) Prior Publication Data

US 2016/0033467 A1 Feb. 4, 2016

(51) Int. Cl.
*G01N 30/62* (2006.01)
*G01N 33/28* (2006.01)
*G01N 33/24* (2006.01)

(52) U.S. Cl.
CPC ........ *G01N 33/2847* (2013.01); *G01N 33/246* (2013.01)

(58) Field of Classification Search
CPC ........................... G01N 33/246; G01N 33/2847
USPC ........................ 73/61.41, 61.43, 61.48, 61.61
See application file for complete search history.

(56) References Cited

U.S. PATENT DOCUMENTS

| | | | |
|---|---|---|---|
| 4,470,301 A * | 9/1984 | Hutchins | B01D 17/0214 210/114 |
| 5,180,221 A | 1/1993 | Yoder | |
| 6,398,382 B1 | 6/2002 | Boyce et al. | |
| 6,793,362 B2 | 9/2004 | Tai | |
| 7,377,151 B1 | 5/2008 | Magee | |
| 2004/0042201 A1 | 3/2004 | Lee | |
| 2007/0025099 A1 | 2/2007 | Urban | |
| 2008/0237503 A1* | 10/2008 | Albertson | G01D 5/262 250/564 |
| 2012/0080372 A1 | 4/2012 | Ries et al. | |

\* cited by examiner

*Primary Examiner* — Benjamin Schmitt
(74) *Attorney, Agent, or Firm* — Procopio, Cory, Hargreaves & Savitch LLP

(57) ABSTRACT

An internal inspection light system for a fuel water separator bowl of a fuel filtration system is disclosed. The internal inspection light system includes an assembly body, a compartment, and a light source. The assembly body is configured to attach to the fuel water separator bowl. The compartment includes a compartment wall extending from the assembly body with at least a portion of the compartment wall being formed of a material such that sufficient light can pass through the compartment wall to illuminate the fuel water separator bowl, and a compartment cap connected to the compartment wall distal to the assembly body. The light source is located within the compartment.

13 Claims, 5 Drawing Sheets

FUEL WATER SEPARATOR BOWL WITH AN INTERNAL INSPECTION LIGHT

TECHNICAL FIELD

The present disclosure generally pertains to a fuel water separator bowl, and is directed toward a fuel water separator bowl with an internal inspection light system.

BACKGROUND

Fuel filters are used to screen out and separate unwanted contaminants, such as water, from the fuel. Fuel water separator bowls are attached to some filters where the contaminants, such as water, are collected. The density of water and other contaminants is generally greater than the density of the fuel which causes the water and other contaminants to settle at the bottom of a fuel water separator bowl. Failure to drain the water and other contaminants in the bowl may allow the water and other contaminants to pass into the engine.

Fuel water separator bowls are inspected on a regular basis to inspect the fuel and to determine if there is a significant quantity of water and other contaminants in the fuel water separator bowl. Fuel water separator bowls are typically made at least partially from a transparent material to allow for visual inspection of the fuel and of the water/contaminants in the bowl. Fuel water separator bowls are often in enclosed areas with limited ambient light. Over time, debris may accumulate on the inner and outer surfaces of the fuel water separator bowls. Further, the materials used for the fuel water separator bowls may become scratched and may darken over time. Any of these factors may reduce or compromise the ability to visually inspect the fuel water separator bowl.

U.S. Patent Application No. 2007/0025099 to G. Urban discloses a collection bowl illuminator including a reflector for positioning flush against the collection bowl of a fuel filter. The reflector has a semi-circular wall with opposed edges that are doubled back upon one another to define a forwardly opening concavity. The semi-circular wall also has opposed ends that are capped by end plates. A bracket is secured to the reflector for releasable attachment to a fuel filter adjacent its collection bowl. An electrical socket is secured within the concavity and can be connected to an electrical current source by a pair of electrical leads extending from it. A light bulb is positioned within the concavity and is connected to the electrical socket so as to receive an electrical current from the electrical current source and be illuminated thereby.

The present disclosure is directed toward overcoming one or more of the problems discovered by the inventors or that is known in the art.

SUMMARY OF THE DISCLOSURE

In one embodiment, an internal inspection light system for a fuel water separator bowl of a fuel filtration system is disclosed. The internal inspection light system includes an assembly body, a compartment, a light source, and a water in fuel sensor. The assembly body is configured to attach to the fuel water separator bowl. The compartment includes a compartment wall extending from the assembly body with at least a portion of the compartment wall being transparent, and a compartment cap connected to the compartment wall distal to the assembly body. The light source is located within the compartment. The water in fuel sensor includes a first sensor component located adjacent a connection between the assembly body and the compartment, and a second sensor component spaced apart from the first sensor component.

DETAILED DESCRIPTION

The systems and methods disclosed herein include a fuel system with a fuel water separator bowl. In embodiments, the fuel water separator bowl includes a light source within the collection area from the bottom of the fuel water separator bowl. The light source internally illuminates the fuel water separator bowl allowing for easier inspection of the fuel quality and of the amount of water/contaminants accumulated within the fuel water separator bowl.

Figure 1:
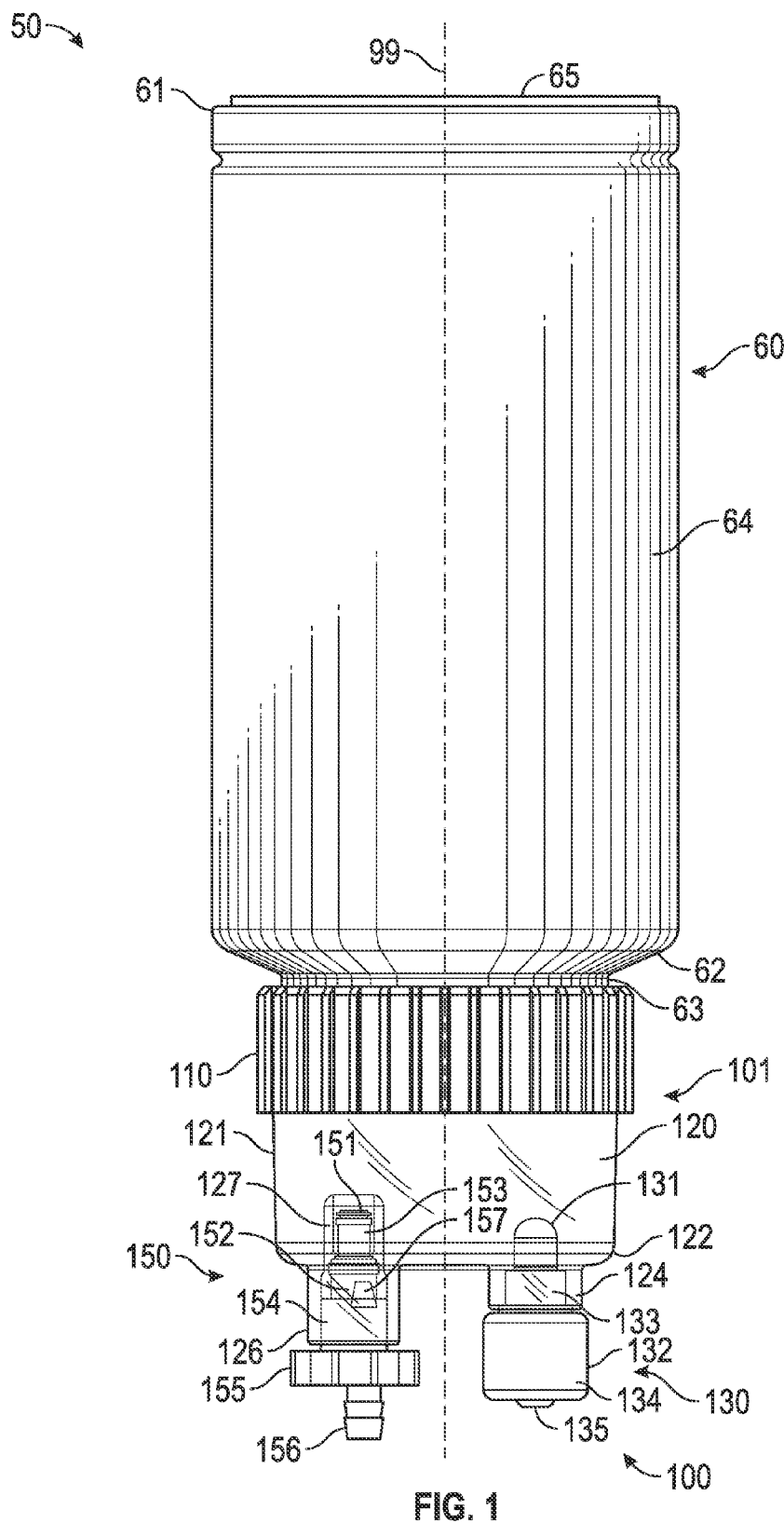
FIG. 1 is a side view of a fuel filtration system.

FIG. 1 is a side view of a fuel filtration system 50. Fuel filtration system 50 may include a fuel filter 60 and a fuel water separator bowl assembly 100. Fuel filter 60 may include a filter casing 64, a top plate 65, and a casing attachment flange 63. Filter casing 64 may be configured to house filter media for filtering contaminants from the fuel. Filter casing 64 may generally include a cylindrical shape, such as a hollow cylinder. Filter casing 64 may also include a casing upper end 61 and a casing lower end 62. Top plate 65 may be disk shaped. Top plate 65 may attach to filter casing 64 at casing upper end 61. In the embodiment illustrated, top plate 65 is separate from filter casing 64.

Casing attachment flange 63 may extend from filter casing 64 at casing lower end 62. Casing attachment flange 63 may extend in the direction opposite casing upper end 61 and may extend along the axis 99 of filter casing 64. In the embodiment illustrated, casing attachment flange 63 is narrower than filter casing 64, having a diameter that is smaller than the diameter of filter casing 64. Casing attachment flange 63 is configured to attach fuel water separator bowl 101 to fuel filter 60. Casing attachment flange 63 may include an attachment mechanism, such as threading.

Fuel water separator bowl assembly 100 may include a fuel water separator bowl 101, an internal inspection light system 130, and a drain assembly 150. Fuel water separator bowl 101 may include a bowl attachment portion 110 and a bowl portion 120. Bowl attachment portion 110 may be configured to attach fuel water separator bowl 101 to fuel filter 60 at casing attachment flange 63 and may be mated to casing attachment flange 63. Bowl attachment portion 110 may include an attachment mechanism, such as threading.

Bowl portion 120 is generally formed of a material, such as a transparent or translucent material, such that sufficient light from light source 131 can pass through bowl portion 120 to allow for visual inspection of the contents within bowl portion 120. Bowl portion 120 may include a bowl wall 121, a bowl bottom 122, a light attaching flange 124, a drain attaching flange 126, and a drain cover 127. Bowl wall 121 is joined to bowl attachment portion 110. Bowl wall 121 may include a hollow cylinder shape. Bowl bottom 122 adjoins bowl wall 121 opposite bowl attachment portion 110. Bowl bottom 122 may include a cylindrical disk shape.

Light attaching flange 124 may extend from bowl bottom 122, away from bowl attachment portion 110, and is configured to receive internal inspection light system 130. Light attaching flange 124 may be a hollow cylinder shape and may include a coupling mechanism, such as threading on its inner surface. Drain attaching flange 126 may extend from bowl bottom 122, away from bowl attachment portion 110, and is configured to receive drain assembly 150. Drain attaching flange 126 may be a hollow cylinder shape and may include a coupling mechanism, such as threading on its inner surface. Drain cover 127 extends from bowl bottom 122, towards bowl attachment portion 110. Drain cover 127 may be a hollow cylinder with a capped end.

Internal inspection light system 130 may include an assembly body 132, a light source 131, and an activation switch 135. Assembly body 132 is configured to attach to fuel water separator bowl 101. In the embodiment illustrated, assembly body 132 attaches to light attaching flange 124 at bowl bottom 122. Assembly body 132 may include a first portion 134 and a second portion 133. First portion 134 may include a cylindrical shape and may include a power source, such as a battery. Second portion 133 may extend from first portion 134 in an axial direction. Second portion 133 may include a coupling mechanism, such as threading on its outer surface for coupling assembly body 132 to fuel water separator bowl 101. Second portion 133 may be configured to mate with light attaching flange 124.

Light source 131 may attach to assembly body 132 and extends at least partially into bowl portion 120. Light source 131 may be a light emitting diode (LED) extending from second portion 133 into bowl portion 120. Light source 131 may include one or more LEDs. Activation switch 135 may connect to light source 131 and to a power source. Activation switch 135 is configured to connect/disconnect the light source 131 to/from the power source to activate/deactivate the light source 131. The color of light emitted by the light source 131 may be selected based on the color of the fuel being filtered, such as white, blue, red, green, yellow, or purple. In some embodiments, more than one color of light may be emitted.

Drain assembly 150 is configured to attach to bowl portion 120 and may attach to drain attaching flange 126 at bowl bottom 122. Drain assembly 150 may include a drain body 152, a drain attachment portion 154, a water exit 157, a drain neck 153, a drain top end 151, a drain flange 155 and a drain outlet 156. Drain body 152 may include a cylindrical shape and may be located within drain attaching flange 126.

Drain attachment portion 154 may extend from drain body 152. Drain attachment portion 154 may include a coupling mechanism, such as threading on its outer surface. Drain attachment portion 154 may be configured to mate with drain attaching flange 126. Drain attachment portion 154 may couple to drain attaching flange 126 with drain body 152 being located between drain attachment portion 154 and drain cover 127. Drain attachment portion 154 may include a diameter greater than the diameter of drain body 152. Water exit 157 may be located in drain body 152 and/or drain attachment portion 154. In the embodiment illustrated, water exit 157 includes a trapezoidal shape extending into drain body 152 and drain attachment portion 154.

Drain neck 153 may extend from drain body 152 in the direction opposite drain attachment portion 154. Drain neck 153 may include a diameter smaller than the diameter of drain body 152. Drain neck 153 extends within drain cover 127. Drain top end 151 may be the end of drain neck 153 distal to drain body 152. Drain top end 151 is located within drain cover 127. Drain top end 151 may include an air hole.

Drain flange 155 may be connected to drain attachment portion 154 and may be located adjacent drain attaching flange 126. Drain flange 155 may include a diameter that is larger than drain attachment portion 154. Drain flange 155 may be configured to provide traction for coupling drain assembly 150 to bowl portion 120.

Drain outlet 156 may extend from drain flange 155. Drain outlet 156 may be configured to couple to outlet tubing for collecting the contaminants, such as water removed from the fuel water separator bowl 101. Drain outlet 156 is in flow communication with water exit 157.

Figure 2:
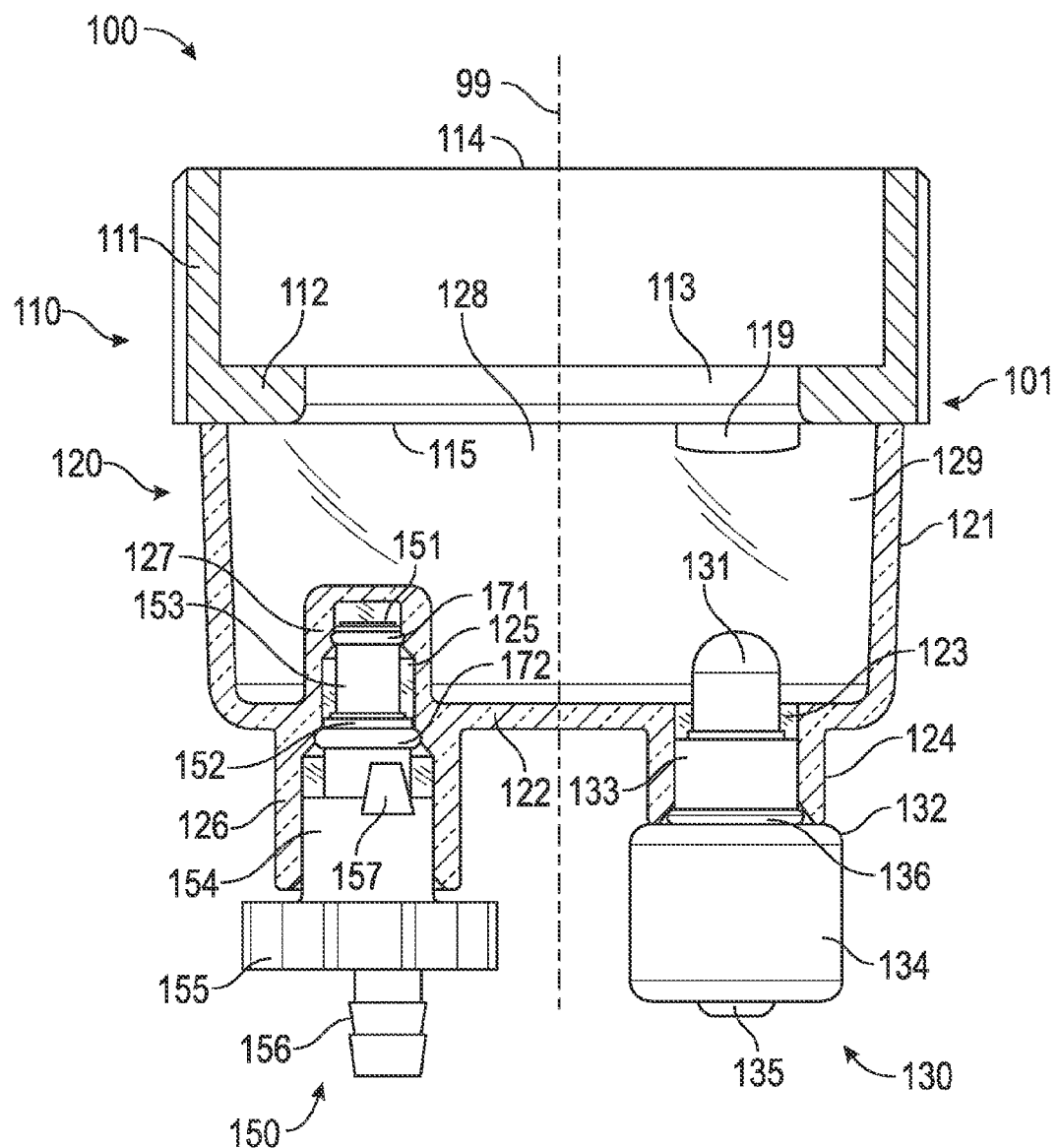
FIG. 2 is a cutaway view of the fuel water separator bowl assembly of the fuel filtration system of FIG. 1.

FIG. 2 is a cutaway view of the fuel water separator bowl assembly 100 of the fuel filtration system 50 of FIG. 1. Bowl attachment portion 110 may include a bowl attachment flange 111 and a bowl annular portion 112. Bowl attachment flange 111 may extend from a bowl attachment portion upper end 114 to a bowl attachment portion lower end 115. Bowl attachment flange 111 may include a hollow cylinder shape located about an axis 99. Bowl attachment flange 111 may include an attachment mechanism, such as threading, on an interior surface for threading fuel water separator bowl 101 to fuel filter 60. Bowl attachment portion upper end 114 may be adjacent to the fuel filter 60 when the fuel water separator bowl 101 is coupled to fuel filter 60.

Bowl annular portion 112 may extend radially inward from bowl attachment flange 111. In the embodiment illustrated, bowl annular portion 112 extends radially inward from bowl attachment flange 111 at bowl attachment portion lower end 115, distal to fuel filter 60. Bowl annular portion 112 may include an annular shape and may form a bowl inlet 113. Bowl inlet 113 allows fluids to pass from fuel filter 60 into fuel water separator bowl 101. Bowl portion 120 may include a bowl upper end 128 distal to bowl bottom 122 that is connected to bowl attachment portion 110. Bowl annular portion 112, bowl wall 121, and bowl bottom 122 may form a containment space 129 for holding contaminants and fuel. Bowl attachment portion 110 and bowl portion 120 may align axially along axis 99.

Bowl portion 120 may also include a light port 123 formed in bowl bottom 122. Light port 123 may be a hole extending through bowl bottom 122 and may include a cylindrical shape. Light attaching flange 124 may extend from bowl bottom 122 adjacent light port 123.

Drain neck 153 and drain cover 127 may be configured to form a drain port 125 there between. Drain port 125 may be an annular space between the drain neck 153 and the drain cover 127. Drain port 125 may be configured to collect fluid from the containment space 129. Drain port 125 is fluidly connected to containment space 129, such as by holes or slots extending through drain cover 127 from containment space 129 to drain port 125.

Fuel water separator bowl assembly 100 may include one or more reflectors 119 located within bowl portion 120. In the embodiment illustrated, a reflector 119 is located above light source 131 and is attached to bowl attachment portion 110 at bowl annular portion 112. Reflector 119 is configured to disperse the light emanating from light source 131 throughout containment space 129. Reflector 119 may be a convex shape, a concave shape, or may include a combination of shapes. The reflector 119 may be a symmetric or an asymmetric shape.

Figure 3:
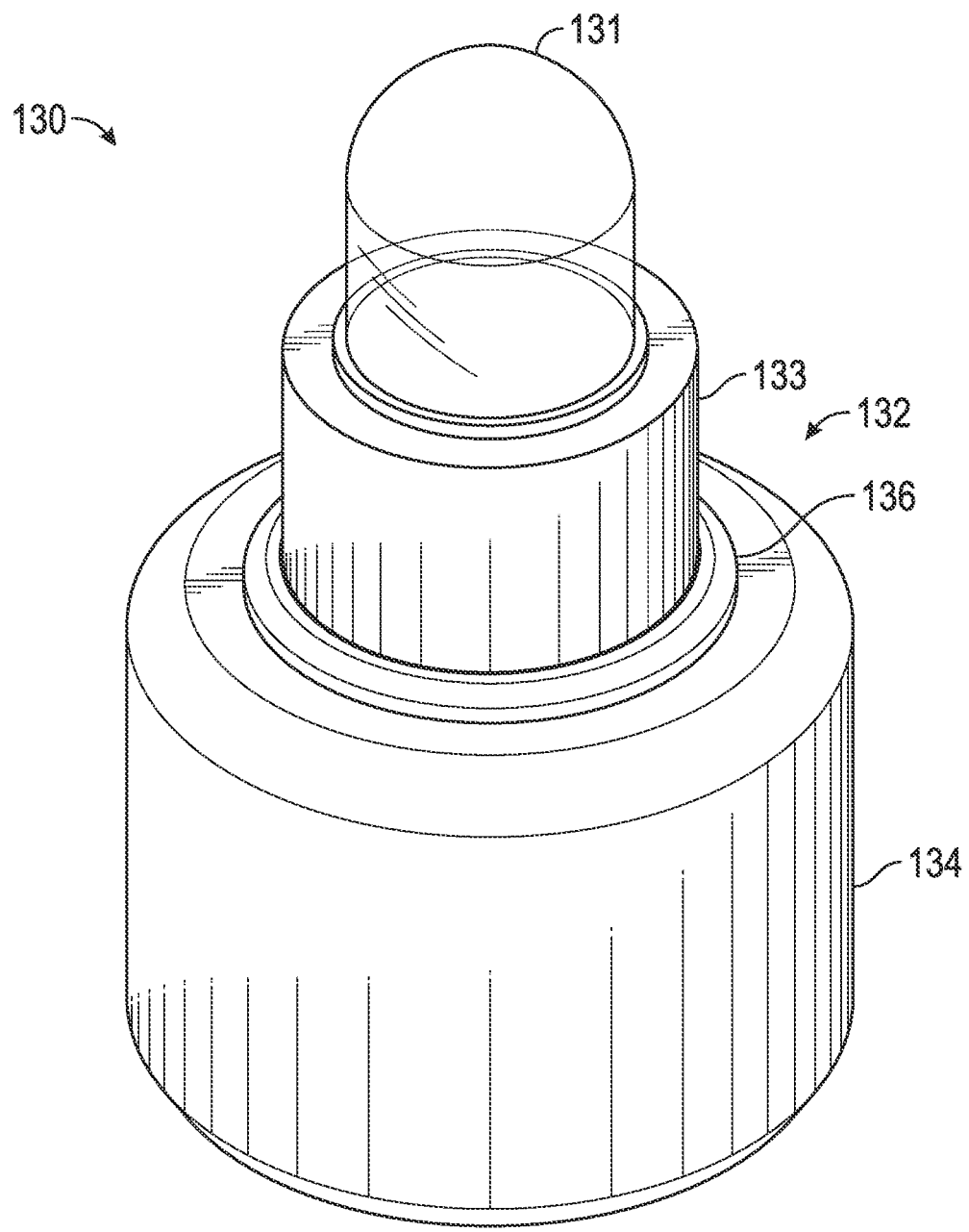
FIG. 3 is a perspective view of the internal inspection light system of FIGS. 1 and 2.

FIG. 3 is a perspective view of the internal inspection light system 130 of FIGS. 1 and 2. Referring to FIGS. 2 and 3, internal inspection light system 130 includes a system seal 136. System seal 136 is configured to form a seal between the assembly body 132 and the fuel water separator bowl 101. In embodiments, the system seal 136 forms a seal with light attaching flange 124. In the embodiment illustrated, system seal 136 is located at the intersection of first portion 134 and second portion 133 and is an integral piece of assembly body 132. In other embodiments, system seal 136 is a separate seal. In some embodiments, system seal 136 is an O-ring seal.

Referring again to FIG. 2, drain assembly 150 may include a first drain seal 171 and a second drain seal 172. First drain seal 171 and second drain seal 172 may be O-ring seals. First drain seal 171 may be located about drain neck 153 adjacent drain top end 151, such as at or near drain top end 151. First drain seal 171 may be configured to form a seal between drain neck 153 and drain cover 127 adjacent drain port 125 when the drain assembly 150 is in a closed position. First drain seal 171 may be located below the air hole located in drain top end 151. First drain seal 171 may block fluid passage to a drain vent. Second drain seal 172 may be located about drain body 152 adjacent drain neck 153 Second drain seal 172 may be configured to form a seal between drain body 152 and bowl portion 120, such as bowl bottom 122 or drain attaching flange 126, when the drain assembly 150 is in a closed position. Second drain seal 172 may also be located adjacent drain port 125, opposite first drain seal 171 when the drain assembly 150 is in a closed position. Second drain seal 172 may be located above water exit 157 and may be configured to block passage of fluid to water exit 157 while second drain seal 172 is in a closed position. In the embodiment illustrated, first drain seal 171 and second drain seal 172 are separate from drain neck 153 and drain body 152 respectively. In other embodiments, first drain seal 171 is integral to drain neck 153 and second drain seal 172 is integral to drain body 152.

Figure 4:
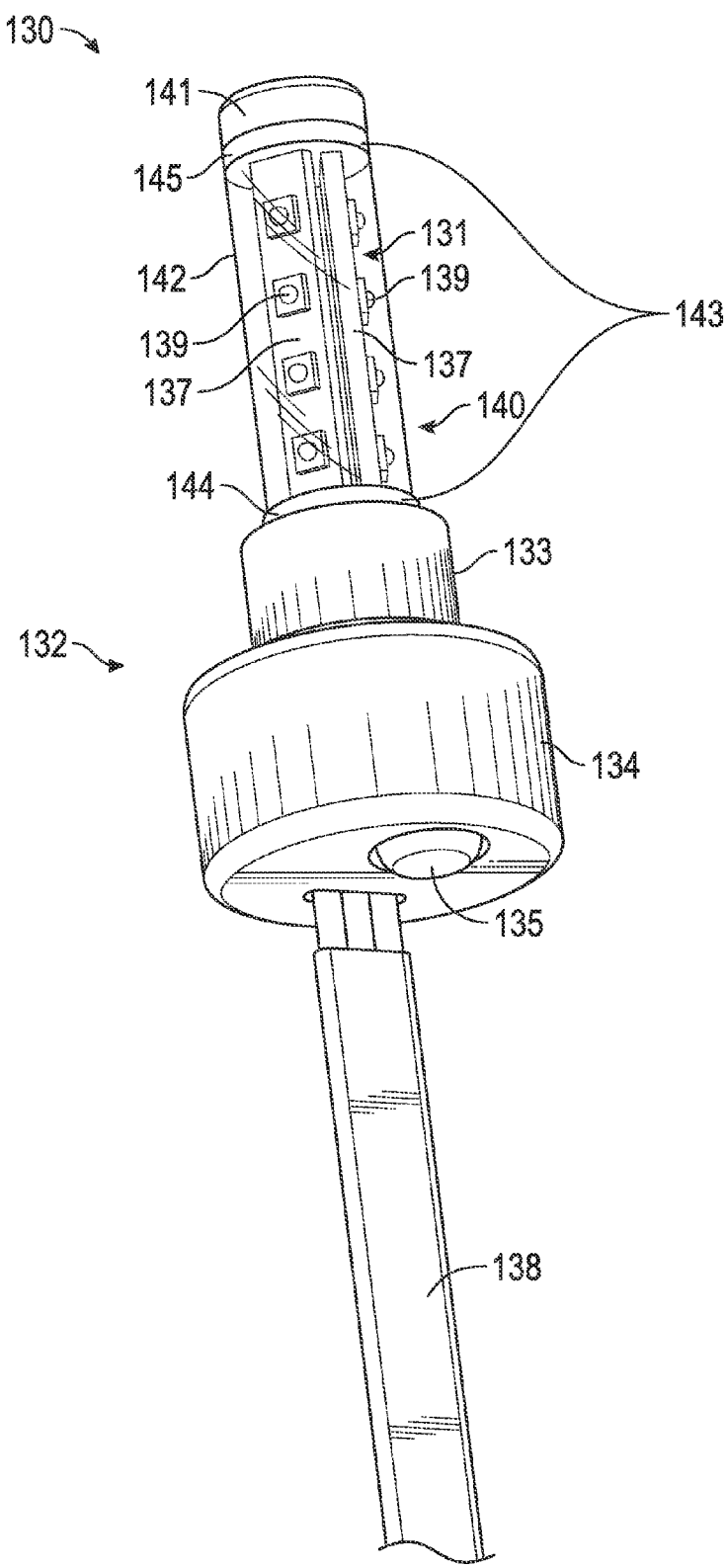
FIG. 4 is a perspective view of an alternate embodiment of the internal inspection light system of FIG. 3.

FIG. 4 is a perspective view of an alternate embodiment of the internal inspection light system 130 of FIG. 3. In the embodiment illustrated in FIG. 4, internal inspection light system 130 includes a compartment 140 extending from assembly body 132. Compartment 140 is configured to extend into bowl portion 120. Compartment 140 includes a compartment wall 142 and a compartment cap 141. Compartment wall 142 may be a hollow cylinder extending from assembly body 132. At least a portion of compartment wall 142 is formed of a material, such as a transparent or translucent material, such that sufficient light from light source 131 can pass through compartment wall 142 to illuminate fuel water separator bowl 101. In other embodiments, all of compartment wall 142 is formed of such a material. Compartment cap 141 is connected to compartment wall 142 distal to assembly body 132. In some embodiments, compartment cap 141 is transparent or translucent, while in other embodiments, compartment cap 141 is opaque.

Light source 131 may include a single light, such as an LED or may include multiple lights, such as LEDs, arranged in a pattern. In the embodiment illustrated in FIG. 4, light source 131 includes one or more LED strips 137 extending within compartment 140. In one embodiment, three LED strips 137 extend within compartment 140. Each LED strip 137 may include multiple LEDs 139. In the embodiment illustrated, each LED strip 137 includes four LEDs 139. In other embodiments, each LED strip 137 may include two, three, five, or more LEDs 139. In some embodiments, the multiple lights are configured to emit the same color of light. In other embodiments, the multiple lights are configured to emit more than one colors of light.

In the embodiment illustrated in FIG. 4, internal inspection light system 130 is includes a water in fuel (WIF) sensor 143. WIF sensor 143 includes a first sensor component 144 and a second sensor component 145. First sensor component 144 may be located adjacent the connection between compartment 140 and assembly body 132 and is configured to be located within containment space 129 adjacent bowl bottom 122. Second sensor component 145 is spaced apart from first sensor component 144 and may be located at compartment cap 141. Second sensor component 145 is configured to be located within bowl portion 120 inside containment space 129 above first sensor component 144. The first sensor component 144 and second sensor component 145 are each connected to an electrical connector, such as a wire. One of the two sensors is a positive terminal, while the other is a negative terminal. When water contacts both terminals it closes the circuit. In some embodiments, the first sensor component 144 is a positive terminal and the second sensor component 145 is a negative terminal. In other embodiments, the first sensor component 144 is a negative terminal and the second sensor component 145 is a positive terminal.

In the embodiment illustrated in FIG. 4, the power source is located remotely from internal inspection light system 130. A power connector 138 connects internal inspection light system 130, including the light source 131 and the WIF sensor 143, to the power source.

Figure 5:
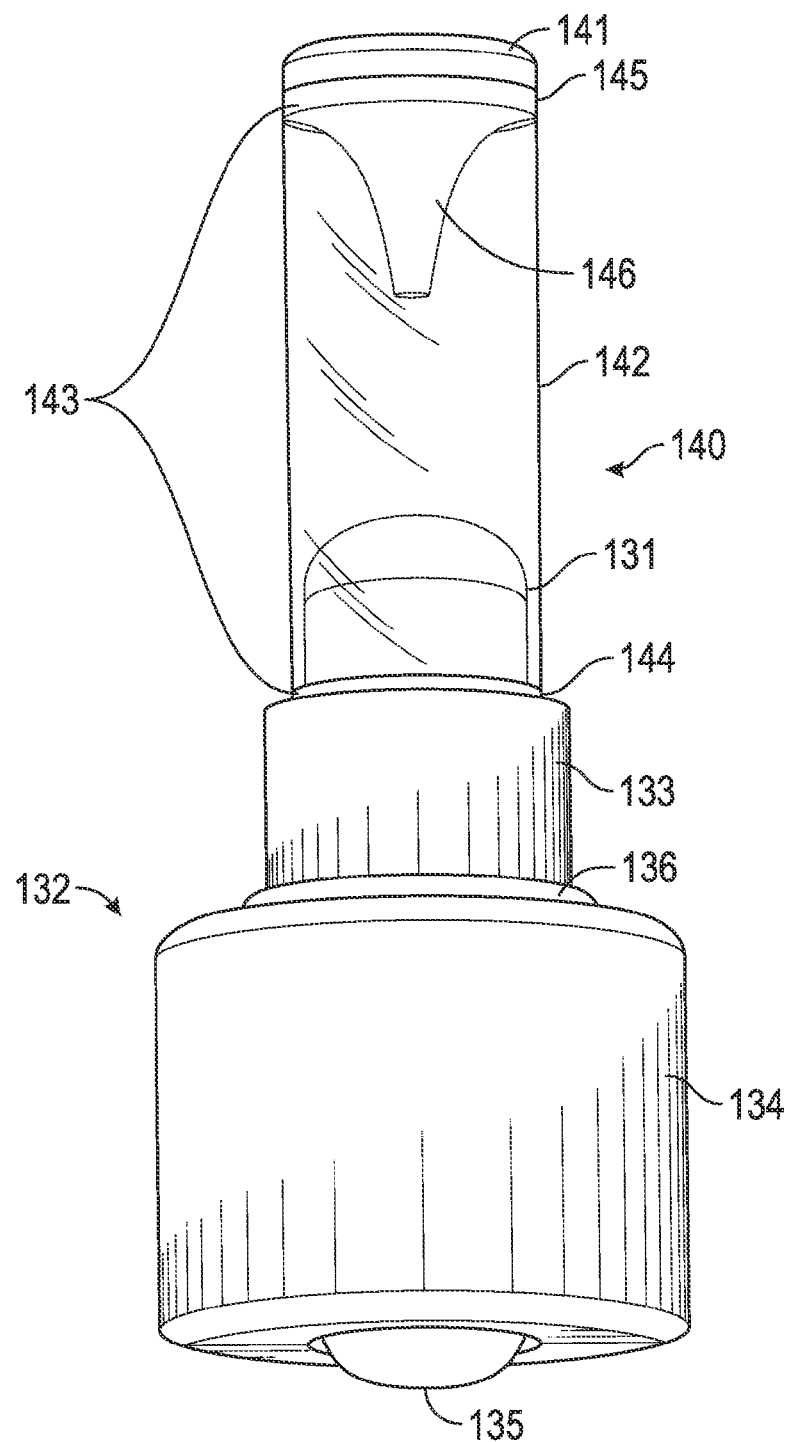
FIG. 5 is a perspective view of an alternate embodiment of the internal inspection light system of FIGS. 3 and 4.

FIG. 5 is a perspective view of an alternate embodiment of the internal inspection light system 130 of FIGS. 3 and 4. In the embodiment illustrated in FIG. 5, compartment 140 includes an integral reflector 146. Integral reflector 146 may extend from compartment cap 141 towards assembly body 132 within compartment wall 142. Integral reflector 146 may be configured to reflect all or a portion of the light directed at integral reflector 146 from the light source 131. Integral reflector 146 may be configured to reflect light throughout containment space 129.

Integral reflector 146 may include a concave shape, a convex shape, a conical shape, or any other shape configured to optimally reflect light within containment space 129. In the embodiment illustrated, integral reflector 146 includes the shape of a portion of a pseudosphere. Integral reflector 146 may be a single surface or may include multiple surfaces. In the embodiment illustrated, integral reflector 146 is a symmetric shape. In other embodiments, integral reflector 146 is an asymmetric shape.

In the embodiment illustrated, an integral reflector 146 is located opposite the light source 131. In other embodiments, multiple integral reflectors 146 may be used to direct light within containment space 129.

INDUSTRIAL APPLICABILITY

Fuel filtration systems filter water and other contaminants out of fuel used within internal combustion engines. Transparent fuel water separator bowls are often used to inspect the fuel and to determine whether there is a significant quantity of contaminants, such as water within the fuel water separator bowl.

Over time the transparent portions of the fuel water separator bowl, such as the bowl wall(s), may become scratched or may collect debris on both the inside and the outside of the fuel water separator bowl. The scratches and/or debris may compromise the ability of a user to inspect the contents of the fuel water separator bowl to determine fuel quality or the presence of contaminants. Fuel water separator bowls are often located in locations within internal combustion engines with little to no ambient light, further compromising the ability of a user to inspect the contents of the fuel water separator bowl.

The fuel water separator bowl 101 including an internal inspection light system 130 may illuminate the contents within the containment space 129 using the light source 131 of the internal inspection light system 130 for improved inspection of the fuel and of the level of contaminants present. The light source 131 may be configured to reflect at the critical angle on the fuel/contaminant interface, which may improve external visibility of the fuel/contaminant interface to detect the amount of contaminants, such as water, within the containment space 129.

In embodiments using LED strips 137, the LED strips 137 can be coupled to the WIF sensor 143 and used as a level indicator for the amount of contaminants, such as water, located within the containment space 129. Reflectors 119, including integral reflectors 146, may disperse the light emanating from the light source 131 throughout the containment space 129 and in particular may direct the light at bowl wall 121 to illuminate the fuel/contaminant interface at bowl wall 121 to further improve inspection of the fuel/contaminant interface.

The color of fuel is not the same in every country. The color of fuel may be any number of colors. Depending on the fuel and its color, different colors of light attenuate at different rates in fluid. In embodiments, one or more colors may be selected to emanate from the light source 131 depending on the color of the fuel to decrease the attenuation of the light and improve the illumination of the fuel water separator bowl 101. In other embodiments, one or more colors may be selected which have a high attenuation to draw out the contrast.

The preceding detailed description is merely exemplary in nature and is not intended to limit the invention or the application and uses of the invention. The described embodiments are not limited to use in conjunction with a particular type of fuel filtration system. Hence, although the present disclosure, for convenience of explanation, depicts and describes a particular fuel filtration system, it will be appreciated that the fuel water separator bowl in accordance with this disclosure can be implemented in various other configurations, and can be used with various other types of fuel filtration systems. Furthermore, there is no intention to be bound by any theory presented in the preceding background or detailed description. It is also understood that the illustrations may include exaggerated dimensions to better illustrate the referenced items shown, and are not consider limiting unless expressly stated as such.

What is claimed is:

1. An internal inspection light system for a fuel water separator bowl of a fuel filtration system, the internal inspection light system comprising:
    an assembly body configured to attach to the fuel water separator bowl;
    a compartment including
        a compartment wall extending from the assembly body, at least a portion of the compartment wall being formed of a material such that sufficient light can pass through the compartment wall to illuminate the fuel water separator bowl, and
        a compartment cap connected to the compartment wall distal to the assembly body;
    a light source located within the compartment; and
    a water in fuel sensor including
        a first sensor component located adjacent a connection between the assembly body and the compartment, and
        a second sensor component located at the compartment cap and spaced apart from the first sensor component.

2. The internal inspection light system of claim 1, wherein the assembly body includes a first portion and a second portion extending from the first portion, the second portion including a coupling mechanism for coupling the assembly body to the fuel water separator bowl.

3. The internal inspection light system of claim 1, further comprising an activation switch configured to connect the light source to a power source.

4. The internal inspection light system of claim 1, wherein the light source includes one or more light emitting diodes.

5. The internal inspection light system of claim 4, further comprising one or more light emitting diode strips, each light emitting diode strip including multiple light emitting diodes.

6. The internal inspection light system of claim 1, wherein the compartment includes an integral reflector extending from the compartment cap towards the assembly body.

7. The internal inspection light system of claim 1, further comprising a system seal configured to form a seal between the assembly body and the fuel water separator bowl.

8. A fuel water separator bowl assembly for a fuel filtration system including a fuel filter, the fuel water separator bowl assembly comprising:
    a fuel water separator bowl including
        a bowl attachment portion for attaching the fuel water separator bowl to the fuel filter, and
        a bowl portion including
            a bowl wall joined to the bowl attachment portion, and
            a bowl bottom adjoining the bowl wall opposite the bowl attachment portion; and
    an internal inspection light system including
        an assembly body attached to the bowl portion, and
        a light source attached to the assembly body and extending at least partially into the bowl portion,
        a compartment extending into the bowl portion, the compartment including a compartment wall extending from the assembly body, at least a portion of the compartment wall being formed of a material such that sufficient light can pass through the compartment wall to illuminate the fuel water separator bowl,
        a compartment cap connected to the compartment wall distal to the assembly body, and
        an integral reflector extending from the compartment cap towards the assembly body.

9. The fuel water separator bowl assembly of claim 8, wherein the light source includes one or more light emitting diodes.

10. The fuel water separator bowl assembly of claim 8, wherein the light source includes light emitting diode strips.

11. The fuel water separator bowl assembly of claim 8, wherein the internal inspection light system includes a water in fuel sensor including a first sensor component located adjacent a connection between the assembly body and the compartment, and a second sensor component spaced apart from the first sensor component and located at the compartment cap.

12. The fuel water separator bowl assembly of claim 8, wherein the internal inspection light system includes a water in fuel sensor including a first sensor component located adjacent the bowl bottom and a second sensor component spaced apart from the first sensor component and located within the bowl portion.

13. The fuel water separator bowl assembly of claim 8, further comprising a reflector located above the light source and within the bowl portion.

\* \* \* \* \*